United States Patent [19]

Johnson et al.

[11] Patent Number: 5,498,824
[45] Date of Patent: *Mar. 12, 1996

[54] METHODS OF PREPARING CUPROUS AND CUPRIC CARBOXYLATES

[75] Inventors: Marvin M. Johnson; Gerhard P. Nowack, both of Bartlesville, Okla.; Ted H. Cymbaluk, Seabrook, Tex.

[73] Assignee: Phillips Petroleum Company, Bartlesville, Okla.

[*] Notice: The term of this patent shall not extend beyond the expiration date of Pat. No. 5,259,986.

[21] Appl. No.: 333,153

[22] Filed: Nov. 1, 1994

Related U.S. Application Data

[62] Division of Ser. No. 815,692, Dec. 31, 1991, Pat. No. 5,371,258.

[51] Int. Cl.$^6$ ............................. C07F 1/08; C07C 7/156
[52] U.S. Cl. .................. 985/848; 585/845; 556/110
[58] Field of Search .......................... 585/845, 848; 502/170, 165; 556/110

[56] References Cited

U.S. PATENT DOCUMENTS

| | | | |
|---|---|---|---|
| 3,360,536 | 12/1967 | McKeon et al. | 260/438.1 |
| 3,514,488 | 5/1970 | Uobele et al. | 260/677 |
| 4,106,917 | 8/1978 | Fields et al. | 55/31 |
| 5,104,570 | 4/1992 | Cymbaluk et al. | 252/182.12 |
| 5,202,521 | 4/1993 | Brown et al. | 585/848 |

OTHER PUBLICATIONS

J. C. Bailar et al., "Comprehensive Inorganic Chemistry", vol. I, p. 963.
J. C. Bailar et al., "Comprehensive Inorganic Chemistry", vol. III, pp. 31–32.
J. W. Mellor, "A Comprehensive Treatise on Inorganic and Theoretical Chemistry", vol. III, p. 158.
Chemical Abstracts, vol. 90, No. 12, p. 619, Abs. No. 96775p published Mar. 19, 1979.

*Primary Examiner*—Asok Pal
*Assistant Examiner*—Bekir L. Yildirim
*Attorney, Agent, or Firm*—Beverly M. Dollar

[57] ABSTRACT

A method for preparing cuprous carboxylates (Cu(I) carboxylates) is provided wherein Cu(II) carboxylates are reacted with copper powder in an aromatic solvent under a reducing atmosphere, optionally in the presence of at least one of a carboxylic acid or carboxylic acid anhydride. Also, a method for preparing desired Cu(II) carboxylates is provided wherein a Cu(II) carboxylate having fewer carbon atoms is reacted with a carboxylic acid corresponding to the desired Cu(II) carboxylate. The invention method reactions achieve good conversions with rapid rates of reaction. The Cu(I) carboxylates produced according to the invention method are useful as reagents or in the preparation of olefin complexing reagents.

3 Claims, No Drawings

METHODS OF PREPARING CUPROUS AND CUPRIC CARBOXYLATES

This application is a division of U.S. application Ser. No. 07/815,692, filed Dec. 31, 1991, (now U.S. Pat. No. 5,317, 258).

FIELD OF THE INVENTION

This invention relates to a process for the preparation of copper (I) carboxylates, hereinafter denoted as Cu(I) carboxylates.

In another aspect, this invention relates to a method of preparing Cu(II) carboxylates.

In another aspect, this invention relates to the preparation of novel compositions useful as olefin complexing reagents.

BACKGROUND OF THE INVENTION

Various methods are known in the literature for preparing Cu(I) carboxylates. In a simple but typical literature preparation, Cu(II) acetate is reduced to Cu(I) acetate in the presence of metallic copper. This reduction reaction is typically an extremely slow reaction with less than complete conversion of the Cu(II) acetate. There exists, therefore, the need for an economical preparation for Cu(I) carboxylates.

Cu(I) carboxylates have been found to be useful, among other things, as complexing reagents employed to separate unsaturated aliphatic hydrocarbons such as olefins from close boiling and difficulty separable saturated aliphatic hydrocarbons such as paraffins.

Various complexing reagents have been described in the prior art. However, difficulties exist with the previously known systems. For example, aqueous systems involving Cu(I) salts and ammonia or ammonium are corrosive and lack necessary long term stability. Non-aqueous Cu(I) solutions using a pyridine solvent have proven difficult to handle due to the solvent and require large scale systems because the reagent is in the form of a slurry in the solvent. Cu(I) sulfonic acid reagents have proven too viscous for easy handling; furthermore the strong heats of adsorption of these salts for olefins render the decomplexation difficult. Finally, Cu(I) salt and Lewis acid systems disclosed in the prior art have evidenced solubility problems and solvent alkylation problems.

There still exists the need for a complexing reagent which has a high olefin complexing capacity while providing for easy desorption of the olefin, has a high solubility in an inert solvent, has a favorable viscosity, is relatively stable, gives few side reactions during the complexing process, and can be prepared from cheap starting materials.

SUMMARY OF THE INVENTION

It is an object of this invention to provide a method for preparing Cu(I) carboxylates from Cu(II) carboxylates.

It is another object of this invention to provide a method for preparing Cu(II) carboxylates.

It is yet another object of this invention to provide complexing agents for the separation of olefins from paraffins, which complexing reagents exhibit good olefin complexing capacity and easy reversibility, and are soluble in an inert solvent.

It is also an object of this invention to provide a method for preparing such complexing reagents from relatively inexpensive starting materials.

It is also an object of this invention to provide a method for separating olefins from a mixture of olefins and paraffins by using the aforementioned complexing reagents.

In accordance with one embodiment of this invention, it has been discovered that Cu(I) carboxylates can be prepared by reacting Cu(II) carboxylates with elemental copper in an aromatic solvent under a reducing atmosphere, optionally in the presence of at least one of a carboxylic acid or carboxylic acid anhydride. The reaction of the invention preparation has been found to proceed at a surprisingly rapid rate with good conversion. The Cu(I) carboxylates prepared by the invention method generally exhibit a high solubility in an inert solvent.

In accordance with another embodiment of this invention, a desired Cu(II) carboxylate is prepared by reacting another Cu(II) carboxylate having fewer carbon atoms with a carboxylic acid corresponding to the desired Cu(II) carboxylate in an aromatic solvent.

The Cu(I) carboxylates prepared according to this invention can be employed as complexing reagents or employed in the preparation of complexing reagents which are useful for separating olefins from olefin and paraffin mixtures.

For example, Cu(I) carboxylates having 8 to 16 carbons atoms prepared according to this invention can be employed as olefin complexing reagents.

Generally, copper (I) carboxylates having fewer than about 8 carbon atoms are only partially soluble in hydrocarbon solvents and are therefore less useful as complexing reagents than the copper (I) carboxylates having 8 or more carbon atoms. However, if the copper (I) carboxylate having fewer than 8 carbon atoms is used in conjunction with at least one high molecular weight olefin having about 10–20 carbon atoms, the copper (I) carboxylate is rendered soluble and still remains active as a complexing reagent.

In another embodiment, complexing reagents are prepared from copper (I) carboxylates associated with high molecular weight olefins having 10 to 20 carbons atoms.

Cu(I) carboxylates prepared according to this invention can be used to prepare a complexing reagent which comprises a copper (I) carboxylate/$BF_3$ adduct in an aromatic solvent. It has further been discovered that the addition of a high molecular weight olefin also enhances the solubility of the adduct in the solvent. The complexing reagents of this invention exhibit the desirable properties of high capacity for olefin adsorption, low viscosity, easy reversibility and absence of side reactions. Thus, olefins can be separated from a mixture of olefins and paraffins by contacting the mixture with the Cu(I) carboxylate-containing complexing reagent under conditions such that the olefin forms an olefin/reagent complex while the paraffins remain uncomplexed. Thereafter, the olefin/reagent complex is treated in order to separate the olefin from the complexing reagent.

DESCRIPTION OF THE PREFERRED EMBODIMENTS

Cu(I) carboxylates are prepared, according to one embodiment of this invention, from corresponding Cu(II) carboxylates by contacting the Cu(II) carboxylate with copper powder in an aromatic solvent under a reducing atmosphere, optionally in the presence of at least one of a carboxylic acid or carboxylic acid anhydride, with a provision for removing any water of reaction or undesired byproducts. Subsequently the Cu(I) carboxylate can be used as a complexing reagent or used directly in the preparation of a Cu(I) carboxylate-containing complexing reagent.

The Cu(II) carboxylates useful in the invention preparation are the Cu(II) salts of mono-, di-, and tri-carboxylic acids containing 1 to about 20 carbon atoms. The carboxylic acid component of the salt can be aliphatic and/or have cyclic or aryl constituents. Suitable examples of Cu(II) carboxylates include but are not limited to Cu(II) acetate, Cu(II) formate, Cu(II) propionate, Cu(II) butyrate, Cu(II) pentanoate, Cu(II) hexanoate, Cu(II) octanoate, Cu(II) decanoate, Cu(II) 2-methyl propionate, Cu(II) methyl formate, Cu(II) ethyl acetate, Cu(II) n-propyl acetate, Cu(II) n-butyl acetate, Cu(II) ethyl propanoate, Cu(II) 2-ethyl hexanoate (Cu(II) octoate), Cu(II) benzoate, and Cu(II) p-t-butyl benzoate. Preferred Cu(II) carboxylates are Cu(II) acetate due to availability and Cu(II) hexanoate due to its high solubility in hydrocarbon solvents.

The carboxylic acids and acid anhydrides useful in the invention preparation are those corresponding to the above listed carboxylates. The carboxylic acid or acid anhydride can be aliphatic and/or have cyclic or aryl constituents. Generally, any carboxylic acid or acid anhydride can be used in the preparation of the Cu(II) carboxylate. The copper (II)carboxylate that is formed as a result of the invention method will usually correspond to the larger chain carboxylic compound used in the preparation, of the copper (II) carboxylate since the more volatile smaller chain carboxylic compound is usually removed during the reaction with the water as an undesired byproduct. The form of the copper II carboxylate can also be controlled to some extent by employing an excess of the reactant with the desired number of carbon atoms. One of ordinary skill in the art can choose the particular components and relative amounts without undue experimentation in order to produce the desired copper (II) carboxylate.

Any carboxylic acid or acid anhydride can be optionally employed in the preparation of the copper (I) carboxylate. In order to minimize side reactions and assure the form of the final copper (I) carboxylate prepared, it is preferred to employ the carboxylic acid or acid anhydride corresponding to the copper (II) carboxylate reactant. The term corresponding is used herein to denote that the carboxylic acid or acid anhydride has the same number of carbon atoms and the same basic backbone structure as the carboxylate. For example, when the copper (II) carboxylate is Cu (II) acetate, the carboxylic acid or acid anhydride used is acetic acid or acetic acid anhydride.

The aromatic solvents useful in this invention are hydrocarbons with unsubstituted or alkyl substituted aryl groups, which are normally in the liquid phase under ambient conditions. Suitable examples include, toluene, xylene, and the like. The aromatic solvent most preferred is xylene. The amount of aromatic solvent generally employed is that which will give a concentration of Cu(I) carboxylate in solution in the range of about 0.005 to about 3 molar.

The Cu(I) carboxylates prepared by the invention method of contacting a Cu(II) carboxylate with copper powder in an aromatic solvent under a reducing atmosphere, optionally in the presence of at least one of a carboxylic acid or acid anhydride are in the form of a clear solution or a slurry of solid carboxylate in the aromatic solvent depending on the solubility of the carboxylate in the solvent. If the form of the product is a solution and it is desired to recover the Cu(I) carboxylate as a solid, the solution can be sparged with an inert gas such as nitrogen in order to remove the reducing atmosphere and thus precipitate the Cu(I) carboxylate. However, the solution of the Cu(I) carboxylate can be used directly as a complexing reagent or used in the preparation of such reagent. If such use is desired, the complexing reagent in solution is preferably stored under the reducing atmosphere. If the final form of the product of the invention is a process slurry, the copper (I) carboxylate can be recovered by removing the solvent, such as by filtration, decantation, vaporization, centrifugation or any other appropriate method known to those skilled in the art.

The carboxylate slurry can be used as the complexing reagent or in the preparation of the reagent; however, it is preferred that the copper (I) carboxylate be soluble in the aromatic solvent if it is to be thus used.

In order to aid the solubility of certain Cu(I) carboxylates in the solvent, a high molecular weight olefin can be added. The high molecular weight olefins useful in this invention are those having about 10 to about 20 carbon atoms. Suitable examples include decene, undecene, dodecene, tridecene, tetradecene, pentadecene, neodene, propylene tetramet, eicosene, and the like. Preferred high molecular weight olefins are propylene tetramet and neodene.

A Lewis acid-containing complexing reagent can be prepared by bubbling or sparging an excess of $BF_3$ through a solution of the Cu(I) carboxylate in an aromatic solvent. The preparation is carried out under an oxygen-free inert atmosphere such as nitrogen and in the essential absence of water. The Cu(I) carboxylate/$BF_3$ adduct is substantially soluble in the aromatic solvent, thus the amount of $BF_3$ which is added to the Cu(I) carboxylate solution is that amount necessary to substantially solubilize the Cu(I) carboxylate. Adduct formation is further generally accompanied by a color change in the solution and in some cases, the formation of two immiscible liquid phases.

Subsequent to the formation of the adduct, excess $BF_3$ is removed, if desired by bubbling or sparging an inert gas such as nitrogen through the solution. The complexing reagent in solution is preferably stored under an inert atmosphere prior to use.

The Cu(I) carboxylate is generally employed in the solvent in a concentration in the range of about 0.005 to 3 molar. It is desirable to have as much of the Cu(I) carboxylate containing complexing reagent contact the olefin-paraffin mixture in solution as possible, therefore it is desirable to have as much Cu(I) carboxylate in the aromatic solvent as can be made soluble. At the same time increased concentrations of Cu(I) carboxylate increase solution viscosity; greater solution viscosity can cause pumping and processing difficulties and is to be avoided if possible. Cu(I) carboxylate concentrations in the range of about 0.01 to about 0.5 molar have given highly satisfactory results and are therefore preferred.

The complexing reagents prepared according to this invention are advantageously employed for the separation of close boiling aliphatic hydrocarbons having from 2 to about 25 carbon atoms, preferably from 2 to about 10 carbons atoms. Such separations include the separation of olefin hydrocarbons from paraffin and/or naphthene hydrocarbons and the separation of diolefin hydrocarbons from paraffin and/or naphthene hydrocarbons. The process of the invention is particularly suitable for separating aliphatic monoolefins from close boiling saturated hydrocarbons. The process is often utilized for the separation of normally gaseous olefins having 2–4 carbon atoms from paraffins and the separation of olefins and cycloolefins having 5–7 carbon atoms from paraffins.

It is also within the scope of this invention to perform a separation of heavier olefins and paraffins which are typically soluble in organic solvents, by choosing an organic solvent in which the olefin/reagent complex is relatively insoluble.

Acyclic and cyclic olefins having from 2 to about 20 carbon atoms per molecule can be separated from paraffins and cycloparaffins by employing the reagent of the invention. Example include ethylene, propylene, the butenes, 2-pentene, cyclopentene, cyclohexene, cycloheptene, 1-heptene, 1-dodecene, 1-eicosene, 3-methyl-1-butene, 4-methyl-1-pentene, 2,3-dimethyl-2-butene, and the like.

The type of separation contemplated in this invention is the separation of alkenes and cycloalkenes from a paraffin or several paraffins, all components of the mixture having similar boiling points. Examples include the separation of ethylene from ethane, propylene from propane, 1-octene from n-octane, cyclohexene from cyclohexane, and the like.

The conditions employed in practicing this invention are selected to allow the olefin to react with the complexing reagent to form the complex while minimizing the problem of separating the nonreacted or noncomplexed portion of the feedstream. In the absorption zone, an absolute pressure ranging from about 0.05 to 20 atmospheres (0.005 to 2 MPa), more preferably from about 0.05 to 2 atmospheres (0.005 to 0.2 MPa), and a temperature ranging from about $-10°$ C. to about $10°$ C. below the boiling point of the solution or slurry of the complexing reagent, preferably from about $30°$ C. to about $25°$ C. below the boiling point of the solution or slurry of the complexing reagent, can be used.

In the desorption zone, the conditions are selected sufficiently different from those used in the absorption zone to promote desorption. Thus, an absolute pressure ranging from about 0.1 to 1.5 atmospheres (0.01 to 0.15 MPa), more preferably from about 0.5 to 1 atmosphere (0.05 to 0.1 MPa), can be employed. The temperature in this zone can range from about $50°$ C. below the boiling point of the solution or slurry of the reagent to the boiling point of the solution or slurry, more preferably from about $30°$ C. below the boiling point of the solution or slurry of the reagent to the boiling point of the solution or slurry.

The following examples are meant to illustrate the invention and should not be taken to limit the scope thereof.

EXAMPLES

EXAMPLE I

This example describes the preparation of Cu(II) octoate, and its use in preparing Cu(I) octoate.

A 15 g (0.075 moles) sample of Cu(II) acetate and 21.7 g (0.15 moles) 2-ethylhexanoic (octanoic) acid were added with 300 cc xylene to a flask equipped with a Dean-Stark trap and a reflux condenser. The mixture was heated to reflux. When the trap became full, its contents were collected and analyzed by gas chromatography (GC). The presence of acetic acid in the analyzed sample confirmed that the reaction was proceeding. The trap was emptied and the contents analyzed several more times during reaction. Fresh xylene was added to the reaction mixture to replace that removed in the analysis procedure. After 3 hours only a trace of acetic acid remained in the trap, so the mixture was cooled to room temperature and a sample was collected from the flash. Upon GC analysis, only traces of acetic and octanoic acid were detected. The solvent was removed by distillation and vacuum transfer. The Cu(II) octoate was then used to prepare Cu(I) octoate as described below.

A 10 g sample of anhydrous Cu(II) octoate (0.028 moles) prepared as described above, 150cc toluene and 3.6g (0.0567 moles) Cu powder was added to a 300cc autoclave. The autoclave was flushed with carbon monoxide (CO) gas and pressurized to 750 psig. No apparent reaction (indicated by CO uptake) occurred after 30 minutes at room temperature so the temperature was increased to $140°$ C. At this temperature CO uptake was observed in the form of pressure decreases and when no further CO uptake occurred, the autoclave was cooled to room temperature. A sample aspirated out of the vessel revealed a partially soluble light blue solid. The solid was air sensitive, turning blue-green almost immediately upon exposure to air. Addition of water to a portion of the sample brought about immediate Cu° metal formation and a dark blue solution, believed to be due to disproportionation. The Cu(I) octoate formed by the reaction above was soluble in the xylene while in the autoclave, but upon carbon monoxide loss became only partially soluble. Thus, upon removal of the Cu(I) octoate from the autoclave a slurry was formed which was stored under a nitrogen atmosphere until further use.

Upon testing in the ethylene absorption apparatus, the Cu(I) octoate complexed with the ethylene in a 1:1 ratio and became soluble in the xylene solvent. Upon decomplexation, a slurry was again formed.

EXAMPLE II

This example describes the preparation of Cu(I) laurate.

A 15 g (0.075 mole) sample of Cu(II) acetate●HO, 30.1 g (0.15 mole) lauric acid and 300cc xylene were added to a flask equipped with a Dean Stark trap. The mixture was heated to reflux and the reaction was monitored by GC as described in Example I. When the reaction was essentially complete, the reaction mixture was cooled to room temperature and the solvent was removed by distillation.

The dark blue product was transferred to a 300cc autoclave and 5.25g (0.83m) Cu powder and 150cc xylene were added. The autoclave was pressurized to 500 psig, heated to $200°$ C. and the reaction was followed by CO uptake. When CO uptake ended, the vessel was cooled to room temperature and a sample of the product aspirated out. It was a bluish waxy solid which was only sparingly soluble in xylene. The product could be solubilized by addition of $BF_3$ which resulted in a light green solution. This solution was shown qualitatively to be active for ethylene adsorption.

EXAMPLE II

This example describes the preparation of Cu(I) Oleate.

Cu(I) oleate (CuOHC) was prepared by the method used in Example II for the preparation of the Cu(I) laurate. The product was isolated as a partially soluble green solution.

EXAMPLE IV

This example describes the basic preparation of the Cu(I) carboxylate, Cu(I) neodecanoate, from the starting materials Cu(II) acetate (Cu(II)(OAc)) and a carboxylic acid in an aromatic solvent.

A 75 g sample of hydrated Cu(II) (OAc) (0.375 moles), 129 g of neodecanoic acid (0.375 moles), and approximately 350 Milliliters xylene were placed in an autoclave equipped with an extraction thimble containing 132 g KCO. The contents of the autoclave were stirred in order to mix them thoroughly and then the autoclave was purged with nitrogen gas. The reactor contents were heated to reflux and both the reactor and the trap were monitored by means of gas chromatography. The reaction was continued until samples taken from the autoclave exhibited only traces of acetic acid and approximately one percent neodecanoic acid. The reaction product, predominantly Cu(II) neodecanoate, was then cooled to room temperature under a nitrogen atmosphere.

Into a clean, dry autoclave were placed 0.375 moles of the Cu(II) neodecanoate produced above in 242 milliliters xylene. The autoclave was then purged with nitrogen gas, and 26.3 grams of Cu powder (0.415 moles) was added. Then the autoclave was pressured with 100 psig of carbon monoxide, and reaction was begun with heating and stirring. The reaction proceeded very quickly, evidenced by a large carbon monoxide uptake (rapid pressure drop). When the pressure drop ceased, the reactor contents were cooled to room temperature and a sample was removed. The blue-green sample turned greener on exposure to the atmosphere, indicating that some disproportion was occurring. The remainder of contents of the autoclave were removed into a 500 milliliter flask under a nitrogen atmosphere. The contents, a blue-green liquid, were heated in the flask to approximately 65° C. while bubbling nitrogen gas through the solution to remove any remaining carbon monoxide. During this process the liquid became a deeper blue and more viscous. In order to reduce the viscosity of the Cu(I) neodecanoate solution, 50 cc of xylene was added. The thus prepared complexing reagent was then tested in the ethylene absorption apparatus and was found to effectively complex 1 equivalent of ethylene.

EXAMPLE V

This example describes the preparation of a Cu(I) acetate (Cu(I) (OAc)) from a corresponding Cu(II) acetate (Cu(II) (OAc)).

A 20 g sample of hydrated Cu(II) (OAc) (0.1 moles), 13 g Cu powder, 12 cc of acetic anhydride, and 88 cc xylene were added to a 300 cc autoclave. The autoclave was flushed with carbon monoxide (CO). The reaction mixture was then stirred at a temperature of 77° F., and monitored for any pressure drop which would indicate that a chemical reaction was taking place. After several minutes, no reaction was observed so the reaction mixture was heated to a temperature of 164° F., at which point the pressure began decreasing. CO uptake, observed in the form of pressure decreases, continued while the temperature rose to approximately 230° F. until about 370 psi of CO had been consumed. At this point no further CO uptake occurred and the autoclave was cooled to room temperature. A small sample of the clear liquid contents of the reactor was removed, however as soon as the sample was exposed to the atmosphere it transformed into a blue solid.

The clear liquid reaction product was vented into two vessels, one of which had been flushed with dry nitrogen, and the other which had been flushed with CO. Upon entering the nitrogen flushed vessel, the clear liquid became cloudy and formed a film on the flask walls. No change in the clear liquid was observed upon its entry into the CO flushed flask, however, later a quantity of white crystals began to form and precipitate from the liquid.

The Cu(I) (OAc) contained in the nitrogen flushed flash was then treated with $BF_3$, causing the producing of two layers of liquid, an upper clear layer and a lower yellow layer. The layers were separated and the yellow layer, when employed as a complexing reagent, was found to absorb approximately two equivalents of ethylene.

EXAMPLE VI

This example describes the preparation of Cu(I) (OAc) from Cu(II) (OAc), using both acetic acid and acetic acid anhydride, where the only solvent present was the acetic acid.

A 20 g sample of Cu(II) (OAc) (0.1m), 7.0 g of Cu powder (0.11 m), 14cc of acetic anhydride, and 86cc of acetic acid were placed in the 300cc autoclave. The autoclave was flushed several times with CO then was pressure to 750 psig with CO. The contents of the autoclave were stirred and the reactor temperature was raised to 120°, at which point CO uptake began. When no further CO uptake occurred, the contents of the autoclave were emptied into a nitrogen flushed flask. The product was a clear, colorless liquid which upon entry into the flask begin to precipitate a white solid. A small amount of the clear liquid which was left in the autoclave turned into a green solid upon exposure to the atmosphere. The contents of the nitrogen flushed flask after setting overnight appeared blue, indicating that the product was more sensitive in the acetic acid solvent than in the xylene solvent used in the other examples.

The Cu(I) (OAc) prepared above was subsequently reacted with $BF_3$ to form a complexing reagent. The reagent was found to complex with 0.37 equivalents of ethylene when tested in the ethylene absorption apparatus.

Although the preparation using acetic acid with no additional solvent gave a Cu(I) (OAc) product, the product was unstable and evidenced some disproportion after sitting overnight. The preparation which took place in the presence of the aromatic solvent, however, was more stable and was useful in the preparation of the complexing reagent.

While this invention has been described in detail for the purpose of illustration, it is not to be construed as limited thereby, but is intended to cover all changes and modifications within the spirit and scope thereof.

That which is claimed is:

1. An olefin complexing reagent which consists essentially of a solution of a branched copper (I) carboxylate having about 8 to about 16 carbon atoms in an aromatic solvent.

2. An olefin complexing reagent in accordance with claim 1 wherein said copper (I) carboxylate is copper (I) neodecanoate, and said aromatic solvent is xylene.

3. An olefin complexing reagent in accordance with claim 1 wherein the concentration of copper (I) carboxylate in said solution is in the range of about 0.005 to about 3.0 molar.

* * * * *